(12) United States Patent
Minami et al.

(10) Patent No.: US 9,656,232 B2
(45) Date of Patent: May 23, 2017

(54) METHOD FOR PRODUCING AROMATIC HYDROCARBONS AND AROMATIC HYDROCARBON PRODUCTION PLANT

(75) Inventors: Hideki Minami, Fujisawa (JP); Yoshishige Sugi, Yokohama (JP); Atsushi Fukui, Kawasaki (JP); Atsuro Nagumo, Kawasaki (JP); Susumu Yasui, Yokohama (JP); Shinichiro Yanagawa, Tokyo (JP)

(73) Assignees: CHIYODA CORPORATION, Kanagawa (JP); JX NIPPON OIL & ENERGY CORPORATION, Tokyo (JP)

( * ) Notice: Subject to any disclaimer, the term of this patent is extended or adjusted under 35 U.S.C. 154(b) by 0 days.

(21) Appl. No.: 13/637,238

(22) PCT Filed: Mar. 25, 2011

(86) PCT No.: PCT/JP2011/057291
§ 371 (c)(1),
(2), (4) Date: Dec. 7, 2012

(87) PCT Pub. No.: WO2011/118750
PCT Pub. Date: Sep. 29, 2011

(65) Prior Publication Data
US 2013/0085310 A1 Apr. 4, 2013

(30) Foreign Application Priority Data
Mar. 26, 2010 (JP) .................................. 2010-072373

(51) Int. Cl.
*C07C 4/06* (2006.01)
*C07C 15/02* (2006.01)
(Continued)

(52) U.S. Cl.
CPC ............... *B01J 8/20* (2013.01); *B01J 29/405* (2013.01); *B01J 35/023* (2013.01); *C07C 4/06* (2013.01);
(Continued)

(58) Field of Classification Search
USPC ........................................................ 585/400
See application file for complete search history.

(56) References Cited

U.S. PATENT DOCUMENTS 3,725,248 A    4/1973 Greenwood et al.
4,066,531 A *  1/1978 Owen et al. ............... 208/120.1
(Continued)

FOREIGN PATENT DOCUMENTS

EP    0259155 B1 *  9/1987
GB    1413067 A     11/1975
(Continued)

OTHER PUBLICATIONS

Barker et al., Kirk-Othmer Encyclopedia of Chemical Technology, 2005, John Wiley and Sons, Inc.*
(Continued)

*Primary Examiner* — In Suk Bullock
*Assistant Examiner* — Youngsul Jeong
(74) *Attorney, Agent, or Firm* — Panitch Schwarze Belisario & Nadel LLP

(57) ABSTRACT

A method for producing aromatic hydrocarbons, the method including: (a) bringing a feedstock oil such as an LCO into contact with an aromatic production catalyst to obtain a reaction product containing aromatic hydrocarbons, (b) separating the reaction product into a tower top fraction and a tower bottom fraction using a distillation tower, (c) separating the tower top fraction into a crude aromatic fraction containing an LPG fraction, and an off-gas containing hydrogen, (d) separating the crude aromatic fraction con-
(Continued)

taining an LPG fraction into an LPG fraction and a crude aromatic fraction, (e) separating the off-gas containing hydrogen into hydrogen and an off-gas, and (f) using the hydrogen obtained in step (e) to hydrotreat the crude aromatic fraction, thereby obtaining an aromatic fraction.

4 Claims, 1 Drawing Sheet

(51) Int. Cl.
*C07C 15/04* (2006.01)
*C07C 15/06* (2006.01)
*B01J 8/20* (2006.01)
*B01J 29/40* (2006.01)
*C10G 35/04* (2006.01)
*C10G 69/10* (2006.01)
*B01J 35/02* (2006.01)
*B01J 21/04* (2006.01)
*B01J 23/882* (2006.01)
*B01J 23/883* (2006.01)
*B01J 23/885* (2006.01)
*B01J 23/888* (2006.01)
*B01J 29/068* (2006.01)
*B01D 3/14* (2006.01)

(52) U.S. Cl.
CPC .............. *C10G 35/04* (2013.01); *C10G 69/10* (2013.01); *B01D 3/143* (2013.01); *B01J 21/04* (2013.01); *B01J 23/882* (2013.01); *B01J 23/883* (2013.01); *B01J 23/885* (2013.01); *B01J 23/888* (2013.01); *B01J 23/8885* (2013.01); *B01J 29/068* (2013.01); *B01J 2229/183* (2013.01); *C10G 2300/1044* (2013.01); *C10G 2300/1059* (2013.01); *C10G 2300/42* (2013.01); *C10G 2400/28* (2013.01); *C10G 2400/30* (2013.01)

(56) References Cited

U.S. PATENT DOCUMENTS

| | | | |
|---|---|---|---|
| 4,936,976 A | 6/1990 | Harandi et al. | |
| 4,971,680 A * | 11/1990 | Kukes | .................... B01J 23/888 |
| | | | 208/111.01 |
| 2009/0314683 A1 * | 12/2009 | Matsushita | ................ 208/111.3 |

FOREIGN PATENT DOCUMENTS

| | | | |
|---|---|---|---|
| GB | 2034351 A | 6/1980 | |
| JP | 48-085605 A | 11/1973 | |
| JP | 49-041323 A | 4/1974 | |
| JP | 53-116328 A | 10/1978 | |
| JP | 03-177496 A | 8/1991 | |
| JP | 03-503656 A | 8/1991 | |
| JP | 03-277692 A | 12/1991 | |
| JP | 2001-279263 A | 10/2001 | |
| JP | 2003-105349 A | 4/2003 | |
| JP | 2005-247959 A | 9/2005 | |
| JP | 2007-100013 A | 4/2007 | |
| JP | 2007-222751 A | 9/2007 | |
| JP | 2007-284565 A | 11/2007 | |
| JP | 2009-040844 A | 2/2009 | |
| JP | 2009-062517 A | 3/2009 | |
| JP | 2009-543899 A | 12/2009 | |
| WO | WO 2006079024 A1 * | 7/2006 | |

OTHER PUBLICATIONS

Int'l Search Report issued May 10, 2011 in Int'l Application No. PCT/JP2011/057291.
Extended European Search Report issued Jan. 28, 2014 in EP Application No. 11759554.6.

* cited by examiner

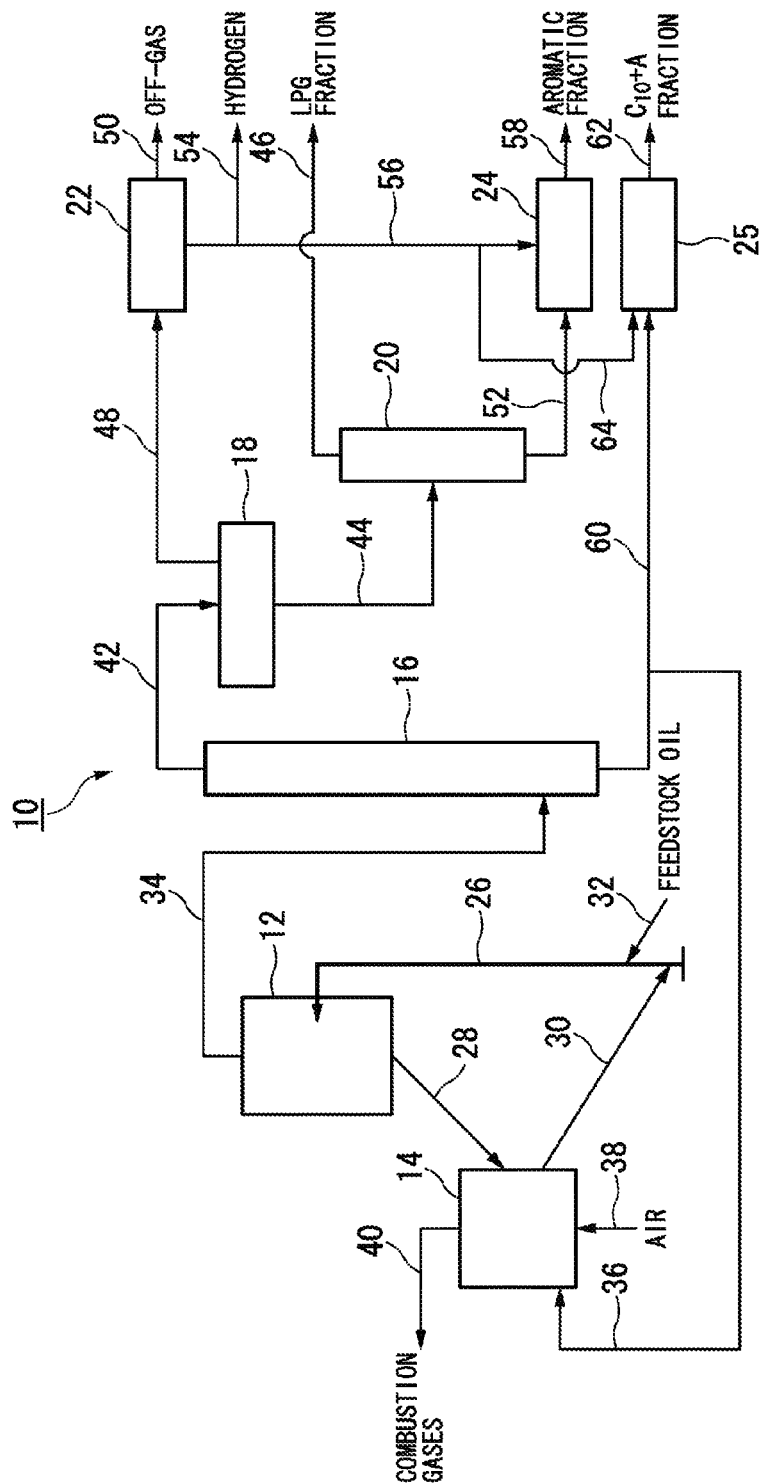

US 9,656,232 B2

METHOD FOR PRODUCING AROMATIC HYDROCARBONS AND AROMATIC HYDROCARBON PRODUCTION PLANT

CROSS-REFERENCE TO RELATED APPLICATIONS

This application is a Section 371 of International Application No. PCT/JP2011/057291, filed Mar. 25, 2011, which was published in the Japanese language on Sep. 29, 2011, under International Publication No. WO 2011/118750 A1 and the disclosure of which is incorporated herein by reference.

BACKGROUND OF THE INVENTION

The present invention relates to a method and a production plant for producing aromatic hydrocarbons by a catalytic aromatic production reaction.

Priority is claimed on Japanese Patent Application No. 2010-72373, filed Mar. 26, 2010, the content of which is incorporated herein by reference.

Methods for producing aromatic hydrocarbons such as BTX (benzene, toluene and xylene) from a feedstock oil such as a light cycle oil (hereinafter also abbreviated as "LCO") obtained from a fluid catalytic cracking (hereinafter also abbreviated as "FCC") apparatus, or a light naphtha or heavy naphtha or the like obtained from a crude oil distillation apparatus, using a catalytic aromatic production reaction that employs an aromatic production catalyst are already well known. These production systems generally employ a fixed bed system (see Patent Document 1), a moving bed system (see Patent Document 2) or a fluidized bed system (see Patent Document 3).

However, feedstock oil such as an LCO obtained from an FCC apparatus, or a light naphtha or heavy naphtha obtained from a crude oil distillation apparatus usually contain a sulfur fraction, and therefore the feedstock oil must be subjected to a preliminary hydrotreatment. Also, the produced crude aromatic fraction including a large amount of BTX contains a sulfur fraction and olefins, and therefore the crude aromatic fraction must be subjected to a hydrotreatment.

However, because hydrogen is required for this type of hydrotreatment, a separate hydrogen production plant must be provided in addition to the aromatic hydrocarbon production plant. As a result, the overall system containing the aromatic hydrocarbon production plant becomes more complex, increasing the production costs for the aromatic hydrocarbons.

CITATION LIST

Patent Documents

[Patent Document 1]
Japanese Unexamined Patent Application, First Publication No. Hei 3-277692
[Patent Document 2]
Japanese Unexamined Patent Application, First Publication No. Sho 48-85605
[Patent Document 3]
Published Japanese Translation of PCT No. H03-503656

BRIEF SUMMARY OF THE INVENTION

The present invention provide a production method and a production plant that does not require the provision of a separate hydrogen production plant for performing hydrotreatment, and can therefore provide aromatic hydrocarbons at low cost.

A method for producing aromatic hydrocarbons according to the present invention includes: (a) bringing one or more feedstock oils selected from the group consisting of light cycle oil obtained from a fluid catalytic cracking apparatus, hydrotreated light cycle oil, and naphtha and straight-run gas oil obtained from a crude oil distillation apparatus into contact with an aromatic production catalyst to obtain a reaction product containing aromatic hydrocarbons, (b) separating the reaction product into a tower top fraction and a tower bottom fraction using a distillation tower, (c) separating the tower top fraction into a crude aromatic fraction containing an LPG fraction, and an off-gas containing hydrogen, (d) separating the crude aromatic fraction containing an LPG fraction into an LPG fraction and a crude aromatic fraction, (e) separating the off-gas containing hydrogen into hydrogen and an off-gas, and (f) using the hydrogen obtained in step (e) to hydrotreat the crude aromatic fraction, thereby obtaining an aromatic fraction.

In step (a), at the same time that the feedstock oil is brought into contact with the aromatic production catalyst, which is in a fluidized bed state inside the fluidized bed reactor, thereby obtaining the reaction product containing aromatic hydrocarbons, a heating fuel that is supplied from externally is preferably combusted in the presence of an oxygen-containing gas, thereby heating the aromatic production catalyst that is extracted from the fluidized bed reactor.

The method for producing aromatic hydrocarbons according to the present invention may also include (g) hydrotreating the tower bottom fraction using the hydrogen obtained in step (e).

An aromatic hydrocarbon production plant according to the present invention includes an aromatic production unit that brings one or more feedstock oils selected from the group consisting of light cycle oil obtained from a fluid catalytic cracking apparatus, hydrotreated light cycle oil, and naphtha and straight-run gas oil obtained from a crude oil distillation apparatus into contact with an aromatic production catalyst to obtain a reaction product containing aromatic hydrocarbons, a first separator that separates the reaction product into a tower top fraction and a tower bottom fraction using a distillation tower, a second separator that separates the tower top fraction into a crude aromatic fraction containing an LPG fraction, and an off-gas containing hydrogen, a third separator that separates the crude aromatic fraction containing an LPG fraction into an LPG fraction and a crude aromatic fraction, a fourth separator that separates the off-gas containing hydrogen into hydrogen and an off-gas, a first hydrotreating unit that hydrotreats the crude aromatic fraction to obtain an aromatic fraction, and a first hydrogen supply unit that supplies the hydrogen obtained in the fourth separator to the first hydrotreating unit.

The aromatic production unit preferably has a fluidized bed reactor, in which the feedstock oil is brought into contact with a fluidized bed-state aromatic production catalyst to obtain the reaction product containing aromatic hydrocarbons, and a heating tank in which the aromatic production catalyst extracted from the fluidized bed reactor is heated by combusting, in the presence of an oxygen-containing gas, a heating fuel that is supplied from externally.

The aromatic hydrocarbon production plant according to the present invention may also include a second hydrotreating unit that hydrotreats the tower bottom fraction, and a second hydrogen supply unit that supplies the hydrogen obtained in the fourth separator to the second hydrotreating unit.

The method for producing aromatic hydrocarbons and the production plant of the present invention do not require the provision of a separate hydrogen production plant for performing hydrotreatment, and can therefore produce aromatic hydrocarbons at low cost.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1 is a schematic structural diagram illustrating one example of an aromatic hydrocarbon production plant according to the present invention.

DETAILED DESCRIPTION OF THE INVENTION

FIG. 1 is a schematic structural diagram illustrating one example of an aromatic hydrocarbon production plant according to the present invention. The production plant 10 includes a fluidized bed reactor 12 (aromatic production unit), a heating tank 14 (aromatic production unit), a distillation unit 16 (first separator), an absorption separator 18 (second separator), a debutanizer 20 (third separator), a PSA unit 22 (fourth separator), a first hydrotreating unit 24, a second hydrotreating unit 25, and a catalyst riser 26. In addition, the production plant 10 is also provided with a first inclined pipe 28, a second inclined pipe 30, a feed pipe 32, a reaction product pipe 34, a fuel pipe 36, an air pipe 38, an exhaust pipe 40, a tower top oil pipe 42, an LPG fraction-containing crude aromatic fraction pipe 44, an LPG fraction pipe 46, a hydrogen-containing off-gas pipe 48, an off-gas pipe 50, a crude aromatic fraction pipe 52, a hydrogen pipe 54, a first hydrogen supply pipe 56 (first hydrogen supply unit), an aromatic fraction pipe 58, a tower bottom oil pipe 60, a $C_{10}$+A fraction pipe 62 ($C_{10}$+A fraction: a fraction containing mainly aromatic hydrocarbons of 10 or more carbon atoms), and a second hydrogen supply pipe 64 (second hydrogen supply unit).

An outlet port for the catalyst riser 26 and an inlet port for the first inclined pipe 28 are connected to the fluidized bed reactor 12. An outlet port for the first inclined pipe 28 and an inlet port for the second inclined pipe 30 are connected to the heating tank 14. An outlet port for the second inclined pipe 30 and an outlet port for the feed pipe 32 are connected to the inlet port for the catalyst riser 26. Moreover, an inlet port for the reaction product pipe 34 is connected to the fluidized bed reactor 12. An outlet port for the reaction product pipe 34 is connected to the distillation unit 16.

An inlet port for the fuel pipe 36 branches from the tower bottom oil pipe 60. An outlet port for the fuel pipe 36 is connected to the heating tank 14.

An outlet port for the air pipe 38 and an inlet port for the exhaust pipe 40 are connected to the heating tank 14. An inlet port for the tower top oil pipe 42 is connected to the top of the distillation tower of the distillation unit 16. An outlet port for the tower top oil pipe 42 is connected to the absorption separator 18.

An inlet port for the LPG fraction-containing crude aromatic fraction pipe 44 is connected to the absorption separator 18. An outlet port for the LPG fraction-containing crude aromatic fraction pipe 44 is connected to the debutanizer 20. An inlet port for the LPG fraction pipe 46 is connected to the top of the debutanizer 20. An inlet port for the hydrogen-containing off-gas pipe 48 is connected to the absorption separator 18. Moreover, an outlet port for the hydrogen-containing off-gas pipe 48 is connected to the PSA unit 22.

An inlet port for the off-gas pipe 50 and an inlet port for the hydrogen pipe 54 are connected to the PSA unit 22. An inlet port for the crude aromatic fraction pipe 52 is connected to the bottom of the debutanizer 20. An outlet port for the crude aromatic fraction pipe 52 is connected to the first hydrotreating unit 24. An inlet port for the first hydrogen supply pipe 56 branches from the hydrogen pipe 54. An outlet port for the first hydrogen supply pipe 56 is connected to the first hydrotreating unit 24.

An inlet port for the aromatic fraction pipe 58 is connected to the first hydrotreating unit 24. An inlet port for the tower bottom oil pipe 60 is connected to the bottom of the distillation tower of the distillation unit 16. An outlet port for the tower bottom oil pipe 60 is connected to the second hydrotreating unit 25.

An inlet port for the $C_{10}$+A fraction pipe 62 is connected to the second hydrotreating unit 25. An inlet port for the second hydrogen supply pipe 64 branches from the first hydrogen supply pipe 56. An outlet port for the second hydrogen supply pipe 64 is connected to the second hydrotreating unit 25.

The aromatic production unit is used for bringing the feedstock oil into contact with the aromatic production catalyst to produce a reaction product containing aromatic hydrocarbons, and includes the fluidized bed reactor 12, the heating tank 14 and the catalyst riser 26. A unit equipped with a fixed bed reactor or a moving bed reactor may also be used as the aromatic production unit. However, in terms of facilitating temperature control and catalyst regeneration, an aromatic production unit equipped with a fluidized bed reactor is preferred in the present invention.

The fluidized bed reactor 12 is used for bringing the feedstock oil into contact with the fluidized bed-state aromatic production catalyst to obtain a reaction product containing a large amount of BTX. The fluidized bed reactor 12 includes a supply port that supplies a vapor of the feedstock oil and the aromatic production catalyst that have been transported through the catalyst riser 26 into the interior of the fluidized bed reactor 12, an extraction port through which the aromatic production catalyst is extracted into the first inclined pipe 28, a cyclone (not shown in the drawing) that separates the reaction product vapor and the aromatic production catalyst, and a discharge port through which the reaction product vapor that has been separated by the cyclone is discharged into the reaction product pipe 34.

The heating tank 14 is used for actively heating the aromatic production catalyst, using not only the heat generated by combustion of the coke adhered to the aromatic production catalyst, but also energy supplied from an external source. In other words, the heating tank 14 is, in itself, a large heating unit. The heating tank 14 includes three supply ports, an extraction port and an exhaust port. The aromatic production catalyst that has been transported through the first inclined pipe 28 is introduced into the interior of the heating tank 14 through the first supply port. The tower bottom oil (heating fuel) supplied from the distillation unit 16 via the fuel pipe 36 is introduced into the interior of the heating tank 14 through the second supply port. Air (oxygen-containing gas) supplied from an air blower via the air pipe 38 is introduced into the interior of the heating tank 14 through the third supply port. The aromatic production catalyst is extracted through the extraction port of the heating tank 14 and into the second inclined pipe 30. Combustion gases generated by the combustion are exhausted through the exhaust port of the heating tank 14 and into the exhaust pipe 40.

The heating tank may have a plurality of stages, such as a two-stage tank. In other words, the heating tank may incorporate two stages, wherein by increasing the heating temperature within the individual heating tanks in a stepwise manner, degradation of the aromatic production catalyst can be suppressed.

The catalyst riser 26 is a pipe-like member that extends in the vertical direction, and has two supply ports. The aromatic production catalyst that has been transported through the second inclined pipe 30 is introduced into the interior of the catalyst riser 26 through the first supply port, and the feedstock oil that has been supplied through the feed pipe 32 is introduced into the interior of the catalyst riser 26 through the second supply port.

The distillation unit 16 (first separator) separates the reaction product into a tower top fraction containing a large amount of BTX and a tower bottom fraction containing a $C_{10}$+A fraction. The distillation unit 16 may include, for example, a distillation tower and a condenser that cools the tower top fraction discharged from the top of the distillation tower. Further, a separate preheating unit that uses the heat of the tower bottom fraction discharged from the bottom of the distillation tower to preheat the feedstock oil supplied to the aromatic production unit through the feed pipe 32 may also be provided.

The absorption separator 18 (second separator) brings the tower top fraction into contact with a circulating liquid (such as the LPG fraction-containing crude aromatic fraction obtained in the absorption separator 18, or the crude aromatic fraction obtained in the debutanizer 20), thereby absorbing the LPG fraction and the crude aromatic fraction contained within the tower top fraction into the circulating liquid, and separating the tower top fraction into a crude aromatic fraction containing an LPG fraction and an off-gas containing hydrogen. The absorption separator 18 may include, for example, a first absorption tower, a second absorption tower, a storage tank, a return pipe and a stripper. In this case, the first absorption tower is used for bringing the tower top fraction into contact with a circulating liquid (the crude aromatic fraction containing an LPG fraction). The second absorption tower is used for bringing the gas discharged from the top of the first absorption tower into contact with a circulating liquid (the crude aromatic fraction). The storage tank temporarily stores the crude aromatic fraction containing an LPG fraction discharged from the respective bottoms of the first absorption tower and the second absorption tower. The return pipe returns the crude aromatic fraction containing an LPG fraction from the storage tank to the first absorption tower as the circulating liquid. The stripper separates absorbed gas from the crude aromatic fraction containing an LPG fraction discharged from the storage tank.

The debutanizer 20 (third separator) separates the crude aromatic fraction containing an LPG fraction into an LPG fraction containing butane and the like, and a crude aromatic fraction containing a large amount of BTX. The debutanizer 20 may include, for example, a distillation tower, and a condenser that cools the LPG fraction discharged from the top of the distillation tower. Further, a separate waste heat boiler that recovers thermal energy from the crude aromatic fraction discharged from the bottom of the distillation tower may also be provided.

The PSA unit 22 (fourth separator) brings the hydrogen-containing off-gas into contact with an adsorbent (such as a zeolite, activated carbon or silica gel) under normal temperature and normal pressure, thereby adsorbing the components of the off-gas other than hydrogen to the adsorbent and enabling collection of a high-purity hydrogen, and subsequently reduces the pressure at normal temperature to purge the off-gas from the adsorbent and regenerate the adsorbent, thus achieving a separation into hydrogen and an off-gas. The PSA unit 22 may include, for example, a plurality of parallel adsorption towers packed with an adsorbent. The term PSA is an abbreviation of "Pressure Swing Adsorption", and this process may also be called a pressure difference adsorption process or a heat-free adsorption process.

The first hydrotreating unit 24 hydrotreats the dienes and the sulfur fraction contained within the crude aromatic fraction, yielding an aromatic fraction. The hydrotreatment is preferably a selective hydrotreatment that suppresses hydrogenation of olefins and selectively reduces dienes and the sulfur fraction. Examples of the selective hydrotreating unit include a unit having a fixed bed reactor packed with a selective hydrogenation catalyst (such as a Co—Mo/$Al_2O_3$ catalyst), or a white clay treatment unit.

The second hydrotreating unit 25 hydrotreats the tower bottom fraction, yielding a $C_{10}$+A fraction that has undergone desulfurization and the like. The hydrotreating unit may include, for example, a fixed bed reactor packed with a hydrogenation catalyst (such as a Co—Mo/$Al_2O_3$ catalyst, Ni—Mo/$Al_2O_3$ catalyst, or Ni—Co—Mo/$Al_2O_3$ catalyst).

The present invention also includes the hydrotreatment of the feedstock supplied to the fluidized bed reactor 12, and this hydrotreatment may be performed using the same hydrogenation catalyst as that used in the above-mentioned second hydrotreating unit.

<Method for Producing Aromatic Hydrocarbons>

Production of aromatic hydrocarbons using the production plant 10 illustrated in FIG. 1 is performed, for example, in the manner described below.

(Step (a))

The feedstock oil, which has been preheated using a preheating unit provided partway along the feed pipe 32, is introduced continuously into the catalyst riser 26 from the feed pipe 32. At the same time, the aromatic production catalyst that has been heated in the heating tank 14 is introduced continuously into the catalyst riser 26 from the second inclined pipe 30, and is transported into the fluidized bed reactor 12 by the vapor of the feedstock oil, which rises up the catalyst riser 26 and acts as a transport medium.

The aromatic production catalyst that is supplied continuously, together with the vapor of the feedstock oil, from the catalyst riser 26 to the fluidized bed reactor 12 is converted to a fluidized bed state by the vapor of the feedstock oil. The feedstock oil vapor and the aromatic production catalyst make contact within this fluidized bed state, yielding a reaction product vapor that contains a large amount of BTX. The reaction product vapor and the aromatic production catalyst are separated by the cyclone, and the reaction product vapor is discharged continuously into the reaction product pipe 34. Coke adheres to the catalyst as a result of the contact with the feedstock oil vapor, and a portion of the partially inactivated aromatic production catalyst is extracted continuously from the fluidized bed reactor 12 into the first inclined pipe 28.

By combusting the heating fuel, which is supplied from an external source through the fuel pipe 36, in the presence of the air (oxygen-containing gas) that is supplied from the air blower through the air pipe 38, the aromatic production catalyst that is introduced continuously into the heating tank 14 from the first inclined pipe 28 is heated continuously to a temperature at least as high as the reaction temperature inside the fluidized bed reactor 12. Further, during this heating, the coke adhered to the aromatic production catalyst also combusts, meaning the aromatic production catalyst undergoes regeneration during the heating process. The combustion gases generated by the combustion are discharged continuously into the exhaust pipe 40. The heated aromatic production catalyst is extracted continuously from the heating tank 14 into the second inclined pipe 30, and is then re-introduced into the catalyst riser 26 from the second inclined pipe 30. In this manner, the aromatic production catalyst is continuously circulated between the fluidized bed reactor 12 and the heating tank 14.

As the feedstock oil, at least one oil selected from the group consisting of LCO obtained from an FCC apparatus, hydrotreated LCO, and naphtha and straight-run gas oil and the like obtained from a crude oil distillation apparatus is used. In those cases where these types of feedstock oils are used, the amount of coke that adheres to the aromatic production catalyst upon contact between the feedstock oil and the aromatic production catalyst may be insufficient to supply the fluidized bed reactor with the necessary amount of heat by combusting the coke. Accordingly, in order to enable efficient and stable production of a reaction product containing aromatic hydrocarbons from the above types of feedstock oils, an aromatic production unit that includes a heating tank is particularly effective.

The aromatic production catalyst contains a crystalline aluminosilicate.

Although there are no particular limitations on the amount of the crystalline aluminosilicate within the aromatic production catalyst, if the total mass of the aromatic production catalyst is deemed 100% by mass, then the amount of the crystalline aluminosilicate is preferably within a range from 10 to 95% by mass, more preferably from 20 to 80% by mass, and still more preferably from 25 to 70% by mass. Provided the amount of the crystalline aluminosilicate is not less than 10% by mass and not more than 95% by mass, a satisfactorily high level of catalytic activity is obtained.

Although there are no particular limitations on the crystalline aluminosilicate, medium pore size zeolites such as zeolites with MFI, MEL, TON, MTT, MRE, FER, AEL and EUO type crystal structures are preferred, and in terms of maximizing the yield of monocyclic aromatic hydrocarbons, pentasil-type zeolites are more preferred, and zeolites with MFI-type and/or MEL-type crystal structures are particularly desirable. MFI-type and MEL-type crystalline aluminosilicates are included within the conventional zeolite structures published by The Structure Commission of the International Zeolite Association (Atlas of Zeolite Structure Types, W. M. Meiyer and D. H. Olson (1978), distributed by Polycrystal Book Service, Pittsburgh, Pa. (USA).

The crystalline aluminosilicate preferably contains gallium and/or zinc, and phosphorus. By including gallium and/or zinc, BTX can be produced more efficiently, and the production of non-aromatic hydrocarbon by-products of 3 to 6 carbon atoms can be suppressed significantly. Further, by also supporting phosphorus on the crystalline aluminosilicate, hydrothermal degradation of the catalyst can be inhibited.

Examples of crystalline aluminosilicates containing gallium and/or zinc include catalysts in which gallium and/or zinc is incorporated within the lattice framework of the crystalline aluminosilicate (crystalline aluminogallosilicates and/or crystalline aluminozincosilicates), catalysts in which gallium and/or zinc is supported on the crystalline aluminosilicate (gallium-supporting crystalline aluminosilicates and/or zinc-supporting crystalline aluminosilicates), and catalysts including both of these forms.

A gallium-supporting crystalline aluminosilicate and/or zinc-supporting crystalline aluminosilicate can obtained by supporting gallium and/or zinc on a crystalline aluminosilicate using a conventional method such as an ion-exchange method or an impregnation method. There are no particular limitations on the gallium source and/or zinc source used in these methods, and examples include gallium salts such as gallium nitrate and gallium chloride, gallium oxide, zinc salts such as zinc nitrate and zinc chloride, and zinc oxide.

A crystalline aluminogallosilicate and/or crystalline aluminozincosilicate has a structure in which $SiO_4$, $AlO_4$ and $GaO_4/ZnO_4$ structures adopt tetrahedral coordination within the framework. These crystalline aluminogallosilicates and/or crystalline aluminozincosilicates can be obtained by gel crystallization via hydrothermal synthesis, by a method in which gallium and/or zinc is inserted into the lattice framework of a crystalline aluminosilicate, or by a method in which aluminum is inserted into the lattice framework of a crystalline gallosilicate and/or crystalline zincosilicate.

The amount of gallium and/or zinc within the aromatic production catalyst, relative to a value of 100% for the total mass of the catalyst, is preferably within a range from 0.01 to 5.0% by mass, and more preferably from 0.05 to 2.0% by mass. If the amount of gallium and/or zinc exceeds 5.0% by mass, then the yield of monocyclic aromatic hydrocarbons tends to decrease. Moreover, if the amount of gallium and/or zinc is less than 0.01% by mass, then the yield of monocyclic aromatic hydrocarbons may decrease.

The aromatic production catalyst may be a catalyst that contains either one of gallium or zinc, or a catalyst that contains both gallium and zinc. Further, the catalyst may also contain one or more other metals in addition to the gallium and/or zinc.

There are no particular limitations on the method used for incorporating phosphorus within the aromatic production catalyst, and examples include methods in which an ion-exchange method or impregnation method or the like is used to support phosphorus on a crystalline aluminosilicate, crystalline aluminogallosilicate or crystalline aluminozincosilicate, methods in which a phosphorus compound is added during synthesis of the zeolite, thereby substituting a portion of the framework of the crystalline aluminosilicate with phosphorus, and methods in which a crystallization promoter containing phosphorus is used during synthesis of the zeolite. Although there are no particular limitations on the phosphate ion-containing aqueous solution used during the above methods, a solution prepared by dissolving phosphoric acid, diammonium hydrogen phosphate, ammonium dihydrogen phosphate or another water-soluble phosphate salt in water at an arbitrary concentration can be used particularly favorably.

Furthermore, the amount of phosphorus within the aromatic production catalyst, relative to a value of 100% for the total mass of the catalyst, is preferably within a range from 0.1 to 10.0% by mass. The lower limit for this range is more preferably 0.5% by mass or greater. Further, the upper limit is more preferably not more than 9.0% by mass, and still more preferably 8.0% by mass or less. By ensuring that the amount of phosphorus supported on the crystalline aluminosilicate is at least 0.1% by mass, the yield of monocyclic aromatic hydrocarbons can be prevented from deteriorating over time, whereas by ensuring that the amount of phosphorus is not more than 10.0% by mass, the yield of monocyclic aromatic hydrocarbons can be increased.

The aromatic production catalyst can be obtained by calcining an above-mentioned phosphorus-supporting crystalline aluminogallosilicate, or a crystalline aluminosilicate having gallium and phosphorus supported thereon. The calcination temperature is preferably within a range from 300 to 900° C.

The heating fuel acts as an additional fuel besides the coke adhered to the aromatic production catalyst, and examples of this heating fuel include fuels supplied from externally (so-called torch oil), such as the tower bottom oil from the distillation unit 16. In terms of avoiding the problem of degradation of the aromatic production catalyst caused by water vapor, the heating fuel is preferably a tower bottom oil having a comparatively large ratio of carbon atoms to hydrogen atoms (C/H).

Examples of the oxygen-containing gas include air and pure oxygen, although air is preferred from an economic viewpoint.

Because the heat required by the aromatic production reaction inside the fluidized bed reactor 12 is supplied by the heated aromatic production catalyst, the heating of the feedstock oil by the preheating unit may be performed to any temperature less than the reaction temperature inside the fluidized bed reactor 12, and is preferably within a range from 150 to 350° C.

The pressure inside the fluidized bed reactor 12 varies depending on the targeted reaction yield, but is preferably within a range from 0.1 to 1.5 MPaG, and more preferably from 0.2 to 1.0 MPaG. Provided the pressure is at least 0.1 MPaG, BTX can be produced efficiently. Provided the pressure is not more than 1.5 MPaG, the amount of light gas by-products generated by cracking can be suppressed.

The lower limit for the reaction temperature inside the fluidized bed reactor 12 is preferably 350° C., more preferably 450° C., and still more preferably 500° C. On the other hand, the upper limit for the reaction temperature is preferably 700° C., and more preferably 600° C. Provided the reaction temperature is at least 350° C., the activity of the aromatic production catalyst reaches a satisfactory level. Provided the reaction temperature is not more than 700° C., excessive cracking reactions can be suppressed.

The lower limit for the contact time between the feedstock oil and the aromatic production catalyst inside the fluidized bed reactor 12 is preferably 5 seconds, more preferably 10 seconds, and still more preferably 15 seconds. On the other hand, the upper limit for the contact time is preferably 300 seconds, more preferably 150 seconds, and still more preferably 100 seconds. Provided the contact time is at least 5 seconds, the aromatic production reaction progresses satisfactorily. Provided the contact time is not more than 300 seconds, the amount of light gas by-products generated by cracking can be suppressed.

The amount of the aromatic production catalyst extracted from the fluidized bed reactor 12 (namely, the circulation amount) is preferably in a range from 5 to 30 tons per 1 ton of the feedstock oil supplied to the fluidized bed reactor 12. This amount is also determined in accordance with the overall heat balance.

The pressure inside the heating tank 14 is preferably higher than the pressure inside the fluidized bed reactor 12 in order to facilitate transport of the heated aromatic production catalyst to the fluidized bed reactor 12.

In the case of a two-stage heating process, if the first heating tank is located in a lower position than the second heating tank, then the pressure inside the first heating tank must be set to a higher pressure than that inside the second heating tank to enable transport of the heated aromatic production catalyst into the second heating tank. The pressure inside the first heating tank 14 is preferably approximately 0.1 MPa higher than the pressure inside the second heating tank, and is preferably at least 0.2 MPa higher, and more preferably 0.9 MPa or greater higher.

The lower limit for the pressure inside the second heating tank is preferably 0.1 MPaG, more preferably 0.2 MPaG, and still more preferably 0.3 MPaG. The upper limit is preferably 0.8 MPaG, more preferably 0.7 MPaG, and still more preferably 0.6 MPaG.

Because the heat required by the aromatic production reaction inside the fluidized bed reactor 12 is supplied by the heated aromatic production catalyst, the temperature inside the heating tank 14 must be at least as high as the reaction temperature inside the fluidized bed reactor 12, and is preferably within a range from 500 to 800° C., and more preferably from 600 to 700° C.

In the case of a two-stage heating process, because the heat required by the aromatic production reaction inside the fluidized bed reactor 12 must be supplied by the heated aromatic production catalyst, the temperature of the first heating tank is preferably at least as high as the reaction temperature inside the fluidized bed reactor 12. Further, in order to suppress hydrothermal degradation of the aromatic production catalyst by the high-temperature water vapor generated upon combustion of the heating fuel, the temperature inside the first heating tank is preferably lower than the temperature inside the second heating tank. Specifically, the temperature inside the first heating tank is preferably not more than 650° C., and more preferably 630° C. or lower.

Because the heat required by the aromatic production reaction inside the fluidized bed reactor 12 is supplied by the heated aromatic production catalyst, the lower limit for the temperature inside the second heating tank is preferably the reaction temperature inside the fluidized bed reactor 12, and is more preferably 500° C., and still more preferably 600° C. In contrast, the upper limit for the temperature is preferably 800° C., and more preferably 700° C.

The amount of the heating fuel supplied to the heating tank 14 (in the case of a tower bottom oil) is preferably within a range from 0.005 to 0.08 tons, per 1 ton of the feedstock oil supplied to the fluidized bed reactor 12, with this amount being determined in accordance with the amount of coke generated and the overall heat balance.

In the case of a two-stage heating process, as a general principle, the total amount of the heating fuel is preferably supplied to the first heating tank.

(Step (b))

The reaction product discharged from the fluidized bed reactor 12 is transported through the reaction product pipe 34 to the distillation unit 16. The reaction product introduced into the distillation unit 16 undergoes fractional distillation inside the distillation tower of the distillation unit 16, and is separated into a tower top fraction containing a large amount of BTX and a tower bottom fraction containing $C_{10}$+A.

(Step (c))

The tower top fraction, which is discharged from the top of the distillation tower of the distillation unit 16 and cooled by a condenser, is transported through the tower top oil pipe 42 to the absorption separator 18. The tower top fraction introduced into the absorption separator 18 is brought into contact with a circulating liquid (the LPG fraction-containing crude aromatic fraction or the crude aromatic fraction) inside the absorption tower of the absorption separator 18, thereby absorbing the LPG fraction and the crude aromatic fraction contained within the tower top fraction into the circulating liquid, and separating the tower top fraction into a crude aromatic fraction containing an LPG fraction and an off-gas containing hydrogen. A portion of the separated crude aromatic fraction containing an LPG fraction is returned to the absorption tower as the circulating liquid.

Step (d))

The crude aromatic fraction containing an LPG fraction discharged from the absorption separator 18 is transported through the LPG fraction-containing crude aromatic fraction pipe 44 into the debutanizer 20. The crude aromatic fraction containing an LPG fraction introduced into the debutanizer 20 undergoes fractional distillation inside the debutanizer 20, and is separated into an LPG fraction containing butane and the like, and a crude aromatic fraction containing a large amount of BTX. The LPG fraction, which is discharged from the top of the debutanizer and cooled by a condenser, is transported through the LPG fraction pipe 46 to a location outside the production plant 10. If necessary, a portion of the crude aromatic fraction discharged from the bottom of the distillation tower may be returned to the absorption tower of the absorption separator 18 as the circulating liquid used in the absorption separator 18.

Step (e))

The off-gas containing hydrogen discharged from the absorption separator 18 is transported through the hydrogen-containing off-gas pipe 48 and into the PSA unit 22. The off-gas containing hydrogen introduced into the PSA unit 22 is brought into contact with the adsorbent inside the adsorption tower of the PSA unit 22, thereby adsorbing the components of the off-gas other than hydrogen to the adsorbent, and following recovery of the resulting high-purity hydrogen, the pressure inside the adsorption tower is reduced at normal temperature to purge the off-gas from the adsorbent and regenerate the adsorbent, thus achieving a separation into hydrogen and an off-gas. The off-gas discharged from the PSA unit 22 is transported through the off-gas pipe 50 to a location outside the production plant 10.

Step (f))

The crude aromatic fraction discharged from the bottom of the debutanizer 20 is transported through the crude aromatic fraction pipe 52 into the first hydrotreating unit 24. Further, a portion of the hydrogen discharged from the PSA unit 22 and transported through the hydrogen pipe 54 to a location outside the production plant 10 is transported through the first hydrogen supply pipe 56 to the first hydrotreating unit 24. The crude aromatic fraction introduced into the first hydrotreating unit 24 is brought into contact with a selective hydrogenation catalyst inside a fixed bed reactor of the first hydrotreating unit 24 in the presence of hydrogen, thereby selectively hydrotreating the crude aromatic fraction to remove the olefins and sulfur fraction and obtain a treated aromatic fraction. The aromatic fraction discharged from the first hydrotreating unit 24 is transported through the aromatic fraction pipe 58 to a location outside the production plant 10.

The hydrotreatment performed in the first hydrotreating unit 24 is preferably performed in accordance with a conventional hydrotreatment method for refined gasoline or the like, using a conventional hydrogenation catalyst. Examples of conventional hydrotreatment methods include the methods disclosed in Japanese Unexamined Patent Application, First Publication No. 2001-279263 and Japanese Unexamined Patent Application, First Publication No. 2009-62517.

In a specific example of the hydrotreatment, the crude aromatic fraction is brought into contact with the hydrogenation catalyst in the presence of hydrogen and under conditions including a temperature of approximately 200 to 350° C., a pressure of 1 to 4 MPa, a liquid hourly space velocity of approximately 1 to 20 $hr^{-1}$, and a hydrogen/hydrocarbon ratio of 50 to 600 liters of hydrogen per 1 liter of hydrocarbons.

Examples of the hydrogenation catalyst include at least partially sulfurized catalysts containing at least one group VIII element and/or at least one group VIB element.

Further, the hydrotreatment is preferably conducted as a multi-stage process including a first hydrotreatment region and a second hydrotreatment region, as described in Japanese Unexamined Patent Application, First Publication No. 2009-62517. In other words, in the first hydrotreatment region, the majority of the sulfur fraction is converted to hydrogen sulfide. On the other hand, in the second hydrotreatment region, the olefins are removed and a desulfurization is performed, while the production of mercaptans and the retention of olefins are suppressed as far as possible.

In order to enable removal of the majority of the sulfur fraction and suppression of the saturation of olefins to an absolute minimum, the conditions within the first hydrotreatment region include a temperature of 260 to 315° C., a pressure of 0.7 to 3.5 MPa, and a liquid hourly space velocity of 0.5 to 10 $hr^{-1}$.

On the other hand, the conditions within the second hydrotreatment region are set so that, in order to suppress the production of mercaptans, the temperature is higher than that of the first hydrotreatment region, namely a temperature of 315 to 398° C., whereas in order to suppress the saturation of olefins to an absolute minimum, the pressure is within a range from 0.7 to 20.0 MPa, and the liquid hourly space velocity is from 0.5 to 15 $hr^{-1}$.

Examples of the hydrogenation catalyst for the first hydrotreatment region include conventional hydrogenation catalysts, and specific examples include catalysts having a group VIII metal (and preferably iron, cobalt or nickel or the like) and a group VI metal (and preferably molybdenum or tungsten) supported on a large surface area carrier such as alumina. Typically, the catalyst includes 0.5 to 20% by mass of the group VIII metal and 1 to 25% by mass of the group VI metal. Examples of other suitable catalysts include zeolite catalysts, and noble metal catalysts in which the noble metal is either palladium or platinum.

Examples of the hydrogenation catalyst for the second hydrotreatment region include catalysts with a lamellar structure or eggshell structure having an internal core and an outer layer containing an active desulfurized metal. Specific examples of the material of the internal core include fire-resistant inorganic oxides such as alpha-alumina, theta-alumina, silicon carbide, zirconia and titania. The material for the outer layer, besides the above-mentioned active desulfurized metal, may include the same refractory inorganic oxide as that used for the internal core, or may also include a non-fire-resistant inorganic oxide.

Step (g))

The tower bottom fraction discharged from the bottom of the distillation tower of the distillation unit 16 is transported through the tower bottom oil pipe 60 to the second hydrotreating unit 25. Further, a portion of the hydrogen discharged from the PSA unit 22 and transported through the hydrogen pipe 54 to a location outside the production plant 10 is transported through the first hydrogen supply pipe 56 and the second hydrogen supply pipe 64 to the second hydrotreating unit 25. The tower bottom fraction introduced into the second hydrotreating unit 25 is brought into contact with a hydrogenation catalyst inside a fixed bed reactor of the second hydrotreating unit 25 in the presence of hydrogen, thereby hydrotreating the tower bottom fraction to obtain a hydrotreated $C_{10}$+A fraction. The $C_{10}$+A fraction discharged from the second hydrotreating unit 25 is transported through the $C_{10}$+A fraction pipe 62 to a location outside the production plant 10. A portion of the contents of the $C_{10}$+A fraction pipe 62 may also be recycled into the fluidized bed reactor 12.

The hydrotreatment in the second hydrotreating unit 25 may be performed in accordance with a conventional kerosene fraction or gas oil fraction hydrotreatment method, using a conventional hydrogenation catalyst. Examples of these conventional hydrogenation catalysts and the hydrotreatment methods using those catalysts include the catalysts and methods disclosed in Japanese Unexamined Patent Application, First Publication No. 2003-105349, Japanese Unexamined Patent Application, First Publication No. 2005-247959, Japanese Unexamined Patent Application, First Publication No. 2007-100013, Japanese Unexamined Patent Application, First Publication No. 2007-222751, and Japanese Unexamined Patent Application, First Publication No. 2007-284565.

The present invention also includes hydrotreatment of the feedstock oil supplied to the fluidized bed reactor 12, and the catalyst and conditions for this hydrotreatment may be selected appropriately from the catalysts and treatment conditions described above for the second hydrotreatment.

In the aromatic hydrocarbon production method and production plant according to the present invention described above, at least one feedstock oil selected from the group consisting of light cycle oil obtained from a fluid catalytic cracking apparatus, hydrotreated light cycle oil, and naphtha and straight-run gas oil obtained from a crude oil distillation apparatus is brought into contact with an aromatic production catalyst to obtain a reaction product containing aromatic hydrocarbons, and therefore the reaction product contains a large amount of by-product hydrogen generated during the aromatic production reaction, namely the dehydrogenation reaction. Because this by-product hydrogen from the reaction product is recovered efficiently via each of the separation steps (separators), and is then used effectively in the hydrotreatment of the crude aromatic fraction recovered from the same reaction product via each of the separation steps (separators), there is no need to provide a separate hydrogen production plant for the hydrotreatment, thus enabling aromatic hydrocarbons to be produced at low cost.

Moreover, in an FCC apparatus, which represents one type of feedstock oil production apparatus, little hydrogen is generated as a by-product, and therefore the hydrogen is not recovered, meaning hydrogen generated within the apparatus cannot be used for hydrotreating the feedstock oil. Accordingly, in an FCC apparatus, a separate hydrogen production plant must be provided for producing the hydrogen for performing preliminary hydrotreatment of the feedstock oil such as an LCO.

EXAMPLES

An example is described below.

Example 1

Using the aromatic hydrocarbon production plant 10 having the structure illustrated in FIG. 1, BTX production was conducted in the aromatic production unit under the operating conditions described below, and based on the resulting data, the amounts of the crude aromatic fraction and hydrogen recovered in each of the subsequent separation steps were determined by calculation.

(Operating Conditions)

Heating temperature of feedstock oil by preheating unit: 200° C.

Supply rate of feedstock oil (vapor) to catalyst riser 26: 1 ton/hr

Pressure inside fluidized bed reactor 12: 0.3 MPaG

Reaction temperature inside fluidized bed reactor 12: 560° C.

Contact time between feedstock oil and aromatic production catalyst inside fluidized bed reactor 12: 18 seconds Pressure inside heating tank 14: 0.35 MPaG Temperature inside heating tank 14: 650° C.

Supply rate of heating fuel to heating tank 14: 0.015 tons/1 ton of feedstock oil Supply rate of air to heating tank 14: 17.2 tons/1 ton of feedstock oil A non-hydrotreated LCO was used as the feedstock oil.

The tower bottom oil obtained from the distillation unit 16 was used as the heating fuel (torch oil).

An aromatic production catalyst containing an MFI-type zeolite (particle dimension: approximately 0.3 μm) having gallium incorporated within the lattice structure was used as the aromatic production catalyst.

During operation, heat was able to supplied efficiently to the fluidized bed reactor 12 by the aromatic production catalyst that had been heated in the heating tank 14, and the reaction product was able to be obtained with good stability and with no significant fluctuation in the temperature inside the fluidized bed reactor 12. The amount of the crude aromatic fraction recovered following each of the subsequent separation steps was 0.35 tons/hr, and the amount of hydrogen recovered was 206 $Nm^3$/hr. It was confirmed that this amount of hydrogen was more than sufficient for hydrotreating the crude aromatic fraction and hydrotreating the tower bottom oil.

INDUSTRIAL APPLICABILITY

The present invention is useful for producing aromatic hydrocarbons using an LCO obtained from an FCC apparatus or a naphtha or the like obtained from a crude oil distillation apparatus as a feedstock.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for producing aromatic hydrocarbons, the method comprising:
   (a) bringing one or more feedstock oils into contact with an aromatic production catalyst to conduct a dehydrogenation reaction to obtain a reaction product containing aromatic hydrocarbons and hydrogen under a pressure range of from 0.1 to 1.5 MPaG, (b) separating the reaction product into a tower top fraction and a tower bottom fraction using a distillation tower, wherein the tower top fraction comprises BTX and the tower bottom fraction comprises a $C_{10}$ aromatics fraction, (c) separating the tower top fraction into an LPG fraction-containing crude aromatic fraction, and an off-gas stream containing the hydrogen produced by the dehydrogenation reaction, (d) separating the LPG fraction-containing crude aromatic fraction into an LPG fraction and a crude aromatic fraction, (e) separating the off-gas stream into hydrogen and an off-gas, and (f) using the hydrogen produced by the dehydrogenation reaction obtained in the step (e) to hydrotreat the crude aromatic fraction, thereby obtaining an aromatic fraction, wherein the one or more feedstock oils is selected from the group consisting of light cycle oil obtained from a fluid catalytic cracking apparatus, hydrotreated light cycle oil, and naphtha and straight-run gas oil obtained from a crude oil distillation apparatus, and wherein the aromatic production catalyst comprises a crystalline aluminosilicate containing gallium and phosphorous having an amount of the phosphorus within a range from 0.1 to 10.0% by mass relative to the total mass of the aromatic production catalyst.

2. The method for producing aromatic hydrocarbons according to claim 1, wherein in the step (a), while the one or more feedstock oils is brought into contact with the aromatic production catalyst in a fluidized bed reactor, a heating fuel that is supplied from externally is combusted in presence of an oxygen-containing gas to heat the aromatic production catalyst extracted from the fluidized bed reactor.

3. The method for producing aromatic hydrocarbons according to claim 1, the method further comprising:

(g) hydrotreating the tower bottom fraction using the hydrogen obtained in the step (e).

4. The method for producing aromatic hydrocarbons according to claim 2, the method further comprising:

(g) hydrotreating the tower bottom fraction using the hydrogen obtained in the step (e).

* * * * *